United States Patent [19]
Naruo et al.

[11] Patent Number: 5,457,997
[45] Date of Patent: Oct. 17, 1995

[54] LASER ULTRASONIC DETECTION METHOD AND APPARATUS THEREFOR

[75] Inventors: Kazuteru Naruo, Kashima; Keisho Arai, Higashi-Ibaraki, both of Japan

[73] Assignee: Doryokuro Kakunenryo Kaihatsu Jigyodan, Tokyo, Japan

[21] Appl. No.: 240,727
[22] PCT Filed: Nov. 22, 1991
[86] PCT No.: PCT/JP91/01607
  § 371 Date: May 11, 1994
  § 102(e) Date: May 11, 1994
[87] PCT Pub. No.: WO93/10445
  PCT Pub. Date: May 27, 1993
[51] Int. Cl.⁶ .......................... G01N 29/04; G01N 21/41
[52] U.S. Cl. .................................... 73/643; 73/657
[58] Field of Search ................... 73/657, 643, 655

[56] References Cited

U.S. PATENT DOCUMENTS

| | | | |
|---|---|---|---|
| 4,512,197 | 4/1985 | von Gutfeld | 73/643 |
| 4,554,836 | 11/1985 | Rudd | 73/657 |
| 4,567,769 | 2/1986 | Barkhoudarian | 73/645 |

FOREIGN PATENT DOCUMENTS 63-58155  3/1988  Japan.

Primary Examiner—Hezron E. Williams
Assistant Examiner—Christine K. Oda
Attorney, Agent, or Firm—Wenderoth, Lind & Ponack

[57] ABSTRACT

A reflector/vibrator plate is irradiated with an ultrasonic generation laser beam to generate an ultrasonic wave therein, and the thus generated ultrasonic wave is transmitted into an object to be inspected. The ultrasonic wave transmitted into the inspection object returns to the reflector/vibrator plate by being reflected by a defect such as a flaw present inside the inspection object, if any, thereby causing a vibration in the reflector/vibrator plate. By detecting this vibration with an ultrasonic detection laser beam, the presence of the defect is detected and located in the inspection object. The ultrasonic flaw detection method can be applied to a variety of inspection objects including reflectors having irregularities on the surface or a poor reflectivity, inspection objects having on the surface thereof an opaque liquid which will not allow transmission of the laser beam therethrough, and inspection objects which do not permit generation of ultrasonic waves with a laser beam.

10 Claims, 4 Drawing Sheets

LASER ULTRASONIC DETECTION METHOD AND APPARATUS THEREFOR

BACKGROUND OF THE INVENTION

1. Technical Field

The present invention relates to an inspection for advanced thermal reactors, fast breeders, light water reactors, plant equipment and other equipment in general, and more particularly it relates to a laser ultrasonic detection method and apparatus therefor which can be applied to in-service inspection as well as to continuous monitoring of specimens to be monitored under operation.

2. Background Art

According to prior art ultrasonic flaw inspection methods, defects such as flaws and the like are inspected by directly irradiating laser beams from ultrasonic generation laser apparatus and ultrasonic detection laser apparatus upon the surface of an inspection object of metal material or the like.

In FIG. 4 which shows an example of the prior art ultrasonic flaw detection, the system has an ultrasonic generation laser apparatus 1, an ultrasonic detection laser apparatus 2, an ultrasonic generation laser beam 3, and an ultrasonic detection laser beam 4. In FIG. 4, reference numeral 5 represents an object for inspection, 6 a flaw, and 7 an ultrasonic wave, respectively.

In FIG. 4, an ultrasonic generation laser beam 3 in a pulse form having a high energy of several tens of mJ to several hundreds of mJ is emitted from the ultrasonic generation laser apparatus 1 to irradiate and heat repeatedly the surface of the object 5 to be inspected so as to generate the ultrasonic wave 7 by causing thermal strain therein. Then, a continuous ultrasonic detection laser beam 4 with a low energy of several mJ is emitted from the ultrasonic detection laser apparatus 2 onto the surface of the object 5 to detect a minute vibration appearing on the surface of the inspection object 5, the vibration being produced when the ultrasonic wave 7 generated by the ultrasonic generation laser beam 3 reaches the surface of the object 5 after reflection from a flaw 6 or, the like.

In the prior art laser ultrasonic flaw detection methods in which both the ultrasonic generation laser beam and the ultrasonic detection laser beam are directly irradiated on the surface of an inspection object, there are the following serious problems before the methods are put into practice, thus presently impeding wide application thereof.

One of the problems is that in detection of ultrasonic signals returning from an object by the ultrasonic detection laser apparatus, when the object has irregularities or undulations on its surface as is the case with most objects, or when reflectivity of light is poor, the reflected laser beam from the object is scattered or attenuated, thereby hampering sufficient light quantities necessary for effective measurement from reaching the ultrasonic detecting laser apparatus, thus eventually rendering the ultrasonic detection thereof impossible.

Another problem is that when it is required to generate an intense ultrasonic wave in an object to be inspected by utilizing an ultrasonic generation laser beam, the power of the ultrasonic generation laser beam must also be increased. Such an increase in power can result in the surface of the object being burned.

Still another problem is that at whatever angle of irradiation an ultrasonic generation laser beam is projected onto the surface of the inspection object, most of the ultrasonic wave thus induced in the inspection object propagates in the direction perpendicular to the surface thereof, thereby allowing only a vertical flaw detection, but inhibiting the angle beam detection which is important in the ultrasonic flaw detection.

Further, there is such a problem that when there exists on the surface of the inspection object an opaque liquid, for example, molten metallic sodium or the like, which prevents transmission of the laser beam therethrough, or when the inspection object is made of a material which prevents easy generation of an ultrasonic wave with a laser beam, the ultrasonic detection cannot be applied thereto.

SUMMARY OF THE INVENTION

The present invention is directed to solving the hereinabove stated problems associated with the prior art.

A main object of the invention is to provide a laser ultrasonic flaw detection method and an apparatus therefor which can prevent burning of the surface of the inspection object and provide the angle beam method ultrasonic flaw detection. The method and apparatus of the present invention are to be particularly preferable for inspection of an object having irregularities on the surface, poor reflectivity of light, or to such cases where an opaque liquid which prevents transmission of laser beams therethrough is present on the surface of the inspection object, or the inspection object is made of such materials that inhibit generation of ultrasonic waves with laser beam.

The laser ultrasonic flaw detection method of the present invention comprises the steps of irradiating a reflector/vibrator plate with an ultrasonic generation laser beam to generate an ultrasonic wave in the reflector/vibrator plate; transmitting the ultrasonic wave to an object to be inspected; receiving at the reflector/vibrator plate a reflected ultrasonic wave which is reflected from a defect such as a flaw or the like inside the inspection object; and detecting with an ultrasonic detection laser beam a vibration induced by the reflected ultrasonic wave in the reflector/vibrator plate.

The laser ultrasonic flaw detection apparatus according to the present invention comprises: an ultrasonic generation laser apparatus for emitting an ultrasonic generation laser beam; a reflector/vibrator plate for generating an ultrasonic wave in response to the laser beam irradiation as well as for inducing a vibration therein in response to an ultrasonic wave returning thereto; and an ultrasonic detection laser apparatus for irradiating the reflector/vibrator plate with a laser beam as well as detecting a reflected laser beam which is modulated by the vibration induced in the reflector/vibrator plate, wherein the ultrasonic wave generated by the vibration of the reflector/vibrator plate is applied to the inspection object and the reflecting ultrasonic wave returning from the inspection object is received by the reflector/vibrator plate.

In the present invention, the reflector/vibrator plate is irradiated with a laser beam in a pulse form emitted from the ultrasonic generation laser apparatus, an ultrasonic wave is generated in the reflector/vibrator plate and the thus generated ultrasonic wave is transmitted to the inspection object. The reflector/vibrator plate receives the reflected ultrasonic wave reflected by the defect such as a flaw or the like, and the induced vibration therein is detected by a continuous laser beam from the ultrasonic detection laser apparatus.

BRIEF DESCRIPTION OF THE DRAWINGS

The invention will be described in further detail with reference to the accompanying drawings, in which.

DETAILED DESCRIPTION OF THE INVENTION

A preferred embodiment of the invention will be described with reference to the drawings.

Figure 1:
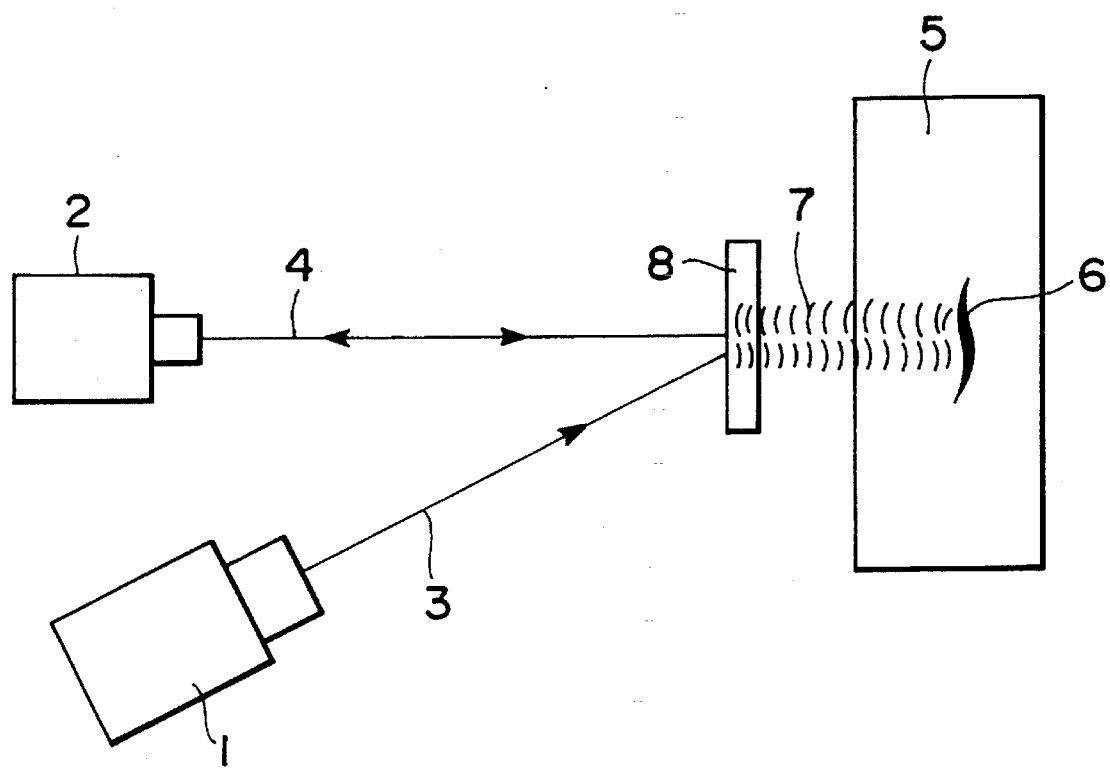
FIG. 1 is a schematic block diagram illustrating the principle of the invention.
Figure 4:
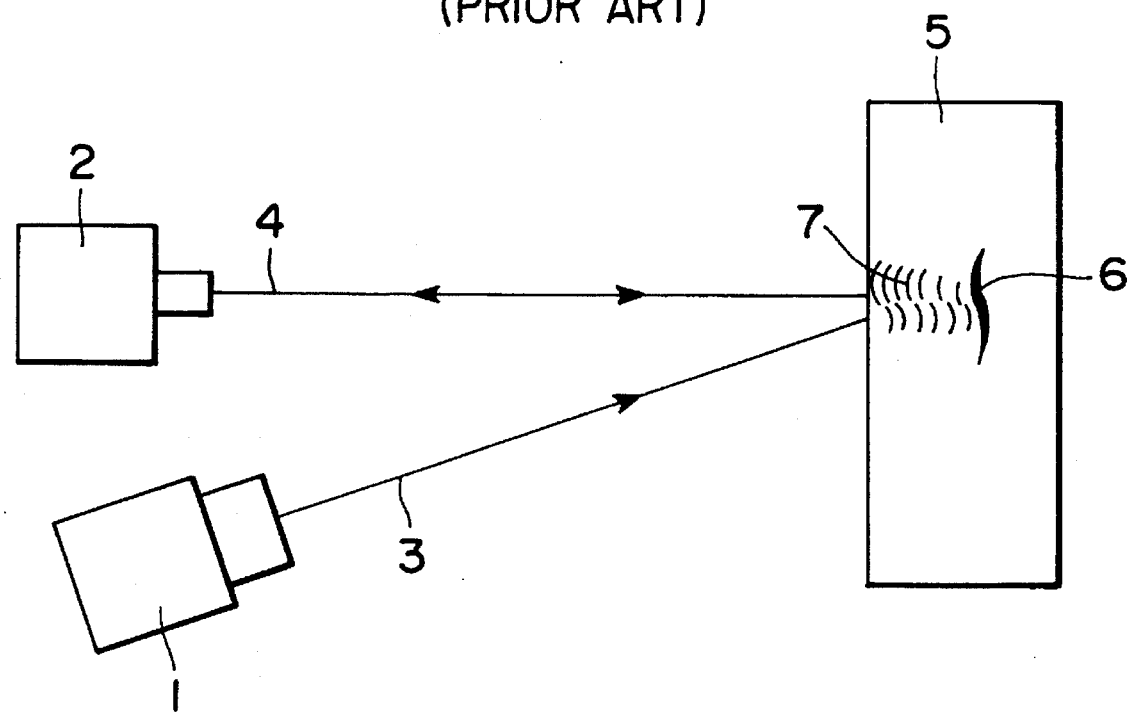
FIG. 4 is a diagram which illustrates a prior art ultrasonic flow detection method.

FIG. 1 illustrates the principle of the invention, in which the same reference numerals as in FIG. 4 are used for same or similar parts, and further, numeral 8 represents a reflector/vibrator plate.

The reflector/vibrator plate 8 in FIG. 1 has a mirror-finished portion for receiving an ultrasonic detection laser beam 4 and a mat-finished portion for receiving on its surface an ultrasonic generation laser beam 3. The mirror-finished portion improves laser beam reflection thereon, and the mat-finished portion is made of a material which readily causes thermal strain by a laser beam irradiation and generates an ultrasonic wave therein.

By the ultrasonic generation laser apparatus 1, a high-energy ultrasonic generation laser beam 3 in pulse form is irradiated onto the surface of the reflector/vibrator plate 8 and, responsive to a repeated heating on the surface by the irradiation, a resulting thermal strain therein generates an ultrasonic wave 7. The thus generated ultrasonic wave 7 propagates in the direction perpendicular to the surface of the reflector/vibrator plate 8, and is transmitted into an inspection object 5. When a defect such as a flaw 6 is present in the object 5, the ultrasonic wave 7 is reflected therefrom and returns to the reflector/vibrator plate 8 to cause a minute vibration therein. The presence of the defect of flaw 6 can be detected by detecting the thus induced vibration with an ultrasonic detecting laser beam 4 emitted from an ultrasonic detection laser apparatus 2.

Figure 2:
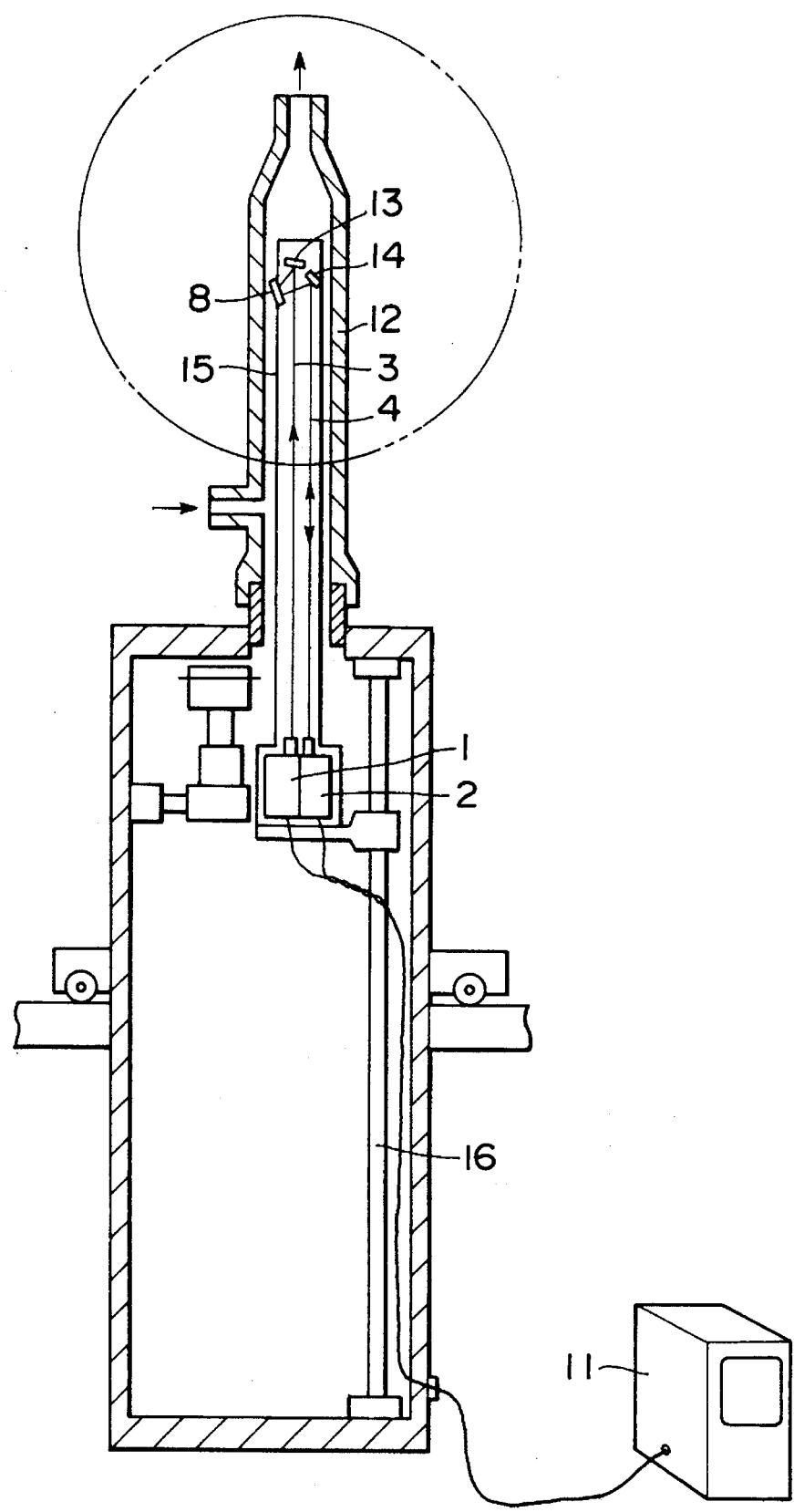
FIG. 2 is a diagram illustrating a schematic arrangement of a laser ultrasonic flaw detection apparatus embodying the invention as applied to inspection of a pressure tube in an advanced thermal reactor.
Figure 3:
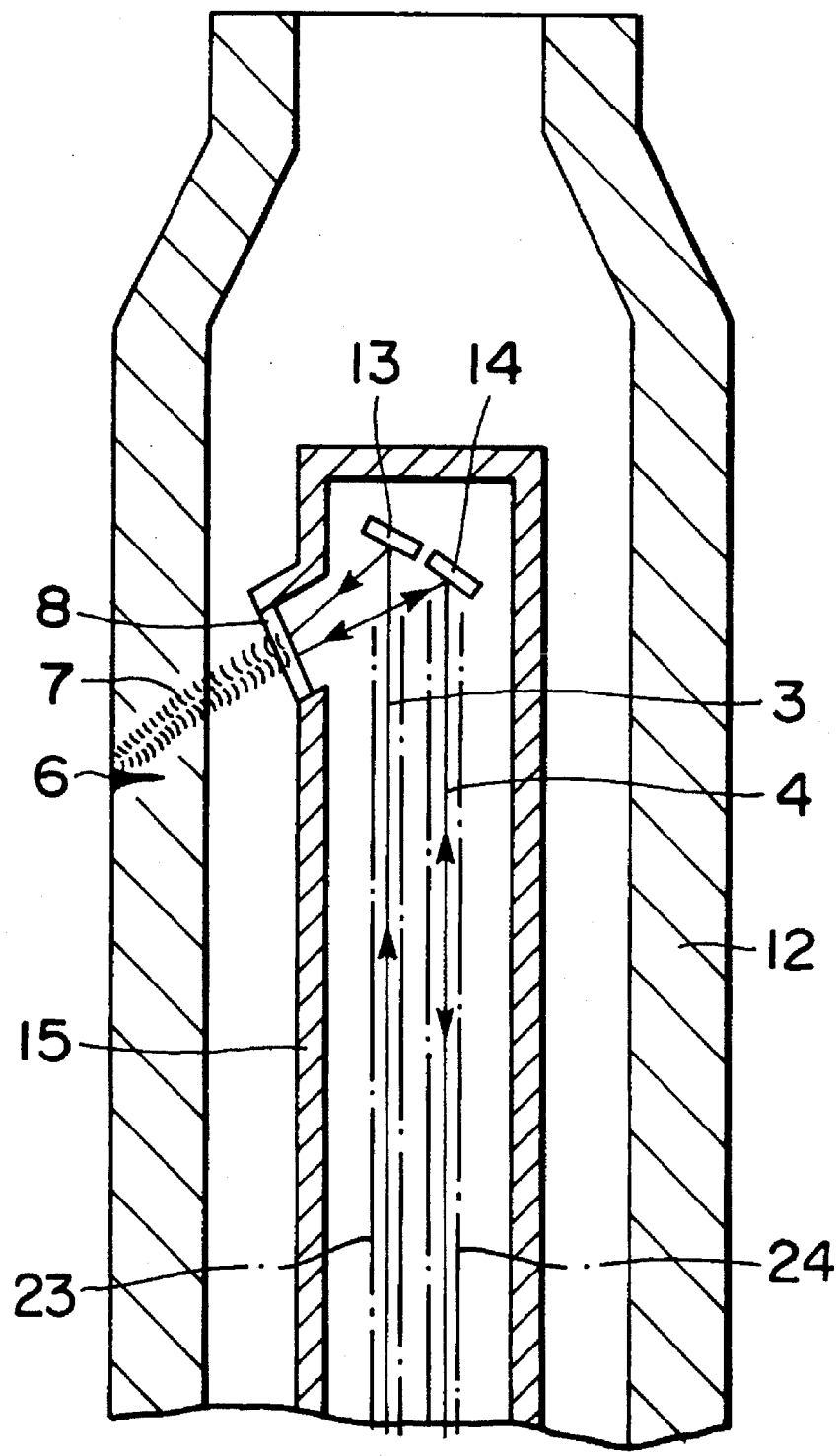
FIG. 3 is an enlarged view of a portion encircled with two-dot chain line in FIG. 2.

FIG. 2 illustrates a schematic arrangement of a laser ultrasonic flaw detection apparatus of the present invention as applied to the inspection of a pressure tube in an advanced thermal reactor. FIG. 3 further shows in detail an enlarged view of a portion pertaining to the invention indicated by the two-dot chain line in FIG. 2. The same reference numerals are used in FIGS. 1–3 to represent the same or similar portions and elements. Further, the illustrated system has a laser ultrasonic flaw detector 11, a pressure tube 12, mirrors 13, 14, optical fibers 23, 24, a sealed tube 15, and a screw rod 16.

In FIG. 2, inside the pressure tube 12, high temperature, high pressure water flows upwardly from the bottom to simulate an inspection condition during operation of the advanced thermal reactor.

The ultrasonic generation laser apparatus 1 and ultrasonic detection laser apparatus 2 are contained inside the sealed tube 15 filled with a gas such as air or the like in order to isolate them from the water, and a reflector/vibrator plate 8 constitutes an ultrasonic transmitter/receiver member. The sealed tube 15 is vertically movable by a screw rod 16 and inserted into the pressure tube 12, so that the sealed tube 15 is set at a predetermined position therein.

With reference to FIG. 2 and 3, an ultrasonic generation laser beam 3 emitted from the ultrasonic generation laser apparatus 1 is reflected by the mirror 13 and then irradiated onto the reflector/vibrator plate 8. Some of the ultrasonic generating laser beam 3 reflected by the reflector/vibrator plate 8 is scattered and attenuated to a nullity, while most of the ultrasonic generation laser beam 3 is absorbed and repeatedly heats up the reflector/vibrator plate 8 to produce a thermal strain therein, thereby generating an ultrasonic wave 7 resulting from the thermal strain. The ultrasonic 7 wave generated in the reflector/virbrator plate 8 propagates in the water in the direction perpendicular to the surface thereof, then is transmitted into the material of the pressure tube 12, and is reflected by a defect such as a flaw or the like, if there exists any, in the pressure tube 12. Then the reflected wave returns to the reflector/vibrator plate 8 causing a small vibration therein.

On the other hand, an ultrasonic detection laser beam 4 emitted from the ultrasonic detection laser apparatus 2 is reflected by the mirror 14 and then irradiated onto the reflector/vibrator plate 8. The ultrasonic detection laser beam 4 is reflected by the reflector/vibrator plate 8 after being modulated therein, and returns via the mirror 14 to the ultrasonic detection laser apparatus 2. Then through analytical processing in the laser ultrasonic flaw detector 11 ultrasonic signals are detected to enable the flaw inspection to be carried out.

The ultrasonic generation laser beam 3 is in a pulse form having energy of several tens to hundreds of mJ, and generally a YAG (yttrium aluminum garnet) laser is utilized for the oscillation thereof. Further, the ultrasonic detection laser beam 4 is a continuous wave form having energy of several mJ, and generally a He—Ne (helium neon) laser is utilized for the oscillation thereof.

As described above, the reflector/vibrator plate 8 is prepared such that it has a mirror-finished surface portion where the ultrasonic detection laser beam 4 irradiates and a mat-finished surface portion where the ultrasonic generation laser beam 3 irradiates. The mirror-finished surface portion has a surface roughness of less than 1 μ m so as to provide improved laser beam reflection, and the mat-finished surface portion facilitates absorption of heat energy and inhibits reflection therefrom. The material of the reflector/vibrator plate 8 is preferably made of a material that reflects laser beams, and generates an ultrasonic wave due to thermal strain when irradiated with a laser beam. The material is preferably metal selected from the group consisting of stainless steel, iron, copper alloys, chromium and the like in view of availability, cost, machinability, resistance to high temperature/pressure, radiation and the like.

Although in the illustrated embodiment of the invention the reflector/vibrator plate 8 is disposed obliquely with respect to the surface of the pressure tube 12 so as to enable an angle beam ultrasonic inspection, it may be disposed parallel to the surface of the pressure tube 12 so as to carry out a vertical ultrasonic inspection.

Further, an appropriate optical fiber laser transmission medium (e.g. optical fibers 23, 24) may be employed for transmission of the ultrasonic generation laser beam 3 and ultrasonic detection laser beam 4 between the ultrasonic generation laser apparatus 1/ultrasonic detection laser apparatus 2 and the reflector/vibrator plate 8.

In a practical use of the present invention, it is preferable to fill a gap between the reflector/vibrator plate and an inspection object with a substance such as water, oil, molten metallic sodium or the like which allows for easy propagation of ultrasonic waves.

As set forth hereinabove, the present invention, provides many advantages and merits as follows.

The laser ultrasonic flaw detection method has become applicable even to inspection objects having irregularities on their surfaces or poor reflectivity for ultrasonic detection laser beams, which have heretofore impeded inspections in the prior art. This applicability of the present invention is due to the fact that the reflected ultrasonic wave reflected by the defect such as flaws in the inspection object is further transmitted to the reflector/vibrator plate 8, and then the mechanical vibration thus produced therein is detected by the ultrasonic detection laser beam. Further, in the prior art method, in the case of an inspection object having different surface reflectivity depending on the place of inspection, even though an ultrasonic detection laser beam has a sufficient reflection intensity, the ultrasonic detection level would change, thereby causing an unreliable inspection. However, according to the present invention the ultrasonic detection laser beam is applied to the same position on the reflector/vibrator plate, and, therefore, stable inspection data can be obtained.

In addition, there is no possibility of burning the inspection object although the reflector/vibrator plate 8 itself is burnt, even when an intense ultrasonic generation laser beam is utilized. Burning of the reflector/vibrator plate, if not too excessive, will not affect the inspection itself, and if too excessive, may necessitate replacement of the expendable reflector/vibrator plate. Further, according to the prior art method, it is quite difficult to carry out a stable inspection even with a constant energy ultrasonic generation laser beam being applied onto the inspection object since the intensity of an ultrasonic wave to be generated therein changes depending changes in energy absorption coefficients due to varying surface conditions. By contrast, according to the present invention, irrespective of the surface conditions of the inspection object, a constant intensity ultrasonic wave can be obtained, thus ensuring a stable inspection. Further, when the surface of the reflector/vibrator plate 8 which receives the ultrasonic generation laser beam has a surface condition which causes reflection to be minimized and energy absorption to be maximized to improve an ultrasonic exchange coefficient, a desired intensity of the ultrasonic waves can be generated with a minimum input of laser energy.

Simply by disposing the reflector/vibrator plate 8 obliquely with respect to the surface of the inspection object, an ultrasonic angle beam inspection method, unrealized by the prior art, can be realized by the present invention.

In a case where opaque liquid metallic sodium, rather than water flows inside the pressure tube 12 of the illustrated embodiment of the invention, it is not possible by the prior art method to carry out the ultrasonic inspection thereof since the ultrasonic generation laser beam is blocked by the liquid metallic sodium. However, provision of the reflector/vibrator plate 8 according to the present invention enables the laser ultrasonic flaw detection to be applied even to such an inspection object having on the surface thereof a liquid which will not allow passage of the ultrasonic generation laser beam.

Still further, since any appropriate material for generating therein an ultrasonic wave with an ultrasonic generation laser beam can be selected for the reflector/vibrator plate 8, laser ultrasonic flaw detection can be applied to inspection object made of materials which present difficulties in generation of an ultrasonic wave with an ultrasonic generation laser beam.

With such advantages and merits being accomplished by the invention, the laser ultrasonic flaw detection method, the application of which has been restricted to very limited types of inspection objects, can now be used in extended range of applications.

In particular, it has become possible for a nuclear reactor, its associated equipment, piping, specimens under monitoring and the like to be monitored continuously and inspected during operation, thereby contributing significantly to the improvement of safety in the operation of a nuclear power generation plant.

What is claimed is:

1. A laser ultrasonic flaw detection apparatus for use in inspecting an object, said apparatus comprising:

an ultrasonic generation laser apparatus for emitting an ultrasonic generation laser beam;

a reflector/vibrator member for receiving the ultrasonic generation laser beam emitted by said ultrasonic generation laser apparatus, for generating an ultrasonic wave and applying the ultrasonic wave to the object in response to receipt of the ultrasonic generation laser beam, for receiving a reflected ultrasonic wave reflected from the object, and for vibrating upon receipt of the reflected ultrasonic wave;

an ultrasonic detection laser apparatus for emitting an ultrasonic detection laser beam to irradiate said reflector/vibrator member, and for detecting a reflected detection laser beam reflected from said reflector/vibrator member and modulated by the vibrating of said reflector/vibrator member; and wherein said reflector/vibrator member has a mat-finished portion where the ultrasonic generation laser beam irradiates, and a mirror-finished portion where the ultrasonic detection laser beam irradiates.

2. A laser ultrasonic flaw detection apparatus according to claim 1, further comprising reflection mirrors for transmitting said ultrasonic generation laser beam and said ultrasonic detection laser beam to said reflector/vibrator member, respectively.

3. A laser ultrasonic flaw detection apparatus according to claim 1, wherein said ultrasonic generation laser beam and said ultrasonic detection laser beam are transmitted to said reflector/vibrator member through an optical fiber.

4. A laser ultrasonic flaw detection apparatus according to claim 1, wherein said reflector/vibrator member is made of a metal material.

5. A laser ultrasonic flaw detector apparatus according to claim 1, wherein said reflector/vibrator member is made of a ceramic material.

6. A laser ultrasonic flaw detection apparatus comprising:

an ultrasonic generation laser apparatus for emitting an ultrasonic generation laser beam;

a reflector/vibrator member for receiving the ultrasonic generation laser beam emitted by said ultrasonic generation laser apparatus, for generating an ultrasonic wave and applying the ultrasonic wave to an object to be inspected in response to receipt of the ultrasonic generation laser beam, for receiving a reflected ultrasonic wave reflected from the object, and for vibrating upon receipt of the reflected ultrasonic wave;

an ultrasonic detection laser apparatus for emitting an ultrasonic detection laser beam to irradiate said reflector/vibrator member, and for detecting a reflected detection laser beam reflected from said reflector/vibrator member and modulated by the vibrating of said reflector/vibrator member; and a pressure tube, said pressure tube constituting the object to be inspected;

a sealed tube disposed movably in an axial direction in said pressure tube; and wherein said reflector/vibrator member comprises a transmitter/receiver member of said sealed tube.

7. A laser ultrasonic flaw detection apparatus according to claim 6, further comprising reflection mirrors for transmitting said ultrasonic generation laser beam and said ultrasonic detection laser beam to said reflector/vibrator member, respectively.

8. A laser ultrasonic flaw detection apparatus according to claim 6, wherein said ultrasonic generation laser beam and said ultrasonic detection laser beam are transmitted to said reflector/vibrator member through an optical fiber.

9. A laser ultrasonic flaw detection apparatus according to claim 6, wherein said reflector/vibrator member is made of a metal material.

10. A laser ultrasonic flaw detector apparatus according to claim 6, wherein said reflector/vibrator member is made of a ceramic material.

* * * * *